US00PP37530P2

(12) United States Plant Patent
Biancheri

(10) Patent No.: US PP37,530 P2
(45) Date of Patent: Jul. 21, 2026

(54) ***RANUNCULUS* PLANT NAMED 'BC ALIGAX'**

(50) Latin Name: *Ranunculus asiaticus x cortusifolius*
Varietal Denomination: BC ALIGAX

(71) Applicant: Biancheri Creazioni Societa' Semplice Agricola, Camporosso Mare (IT)

(72) Inventor: Alberto Biancheri, Camporosso Mare (IT)

(73) Assignee: Biancheri Creazioni Societa' Semplice Agricola (IT)

( * ) Notice: Subject to any disclaimer, the term of this patent is extended or adjusted under 35 U.S.C. 154(b) by 0 days.

(21) Appl. No.: 19/357,329

(22) Filed: Oct. 14, 2025

(51) Int. Cl.
*A01H 6/72* (2018.01)
*A01H 5/02* (2018.01)

(52) U.S. Cl.
USPC ..... Plt./263.1

(58) Field of Classification Search
USPC ..... Plt./263.1
CPC ..... A01H 6/72; A01H 5/02
See application file for complete search history.

*Primary Examiner* — Keith O. Robinson

(57) ABSTRACT

A new and distinct cultivar of *Ranunculus* plant named 'BC ALIGAX' is disclosed characterized by a novel flower form; double daisy-like flowers on well branched flower stems. Flower petals are Pale Yellow Green RHS 157A and 157B. Flower stems are 6 to 20 cm long. The new variety is a *Ranunculus* normally produced as a cut flower and potentially useful as an ornamental plant.

3 Drawing Sheets

Latin name of the genus and species: *Ranunculus asiaticus* x *cortusifolius*.

Variety denomination: 'BC ALIGAX'.

Co-pending application Ser. No. 19/357,296

BACKGROUND OF THE INVENTION

The new *Ranunculus* cultivar is a product of a planned breeding program conducted by the inventor, Alberto Biancheri at a research nursery in Camporosso Mare, Italy. The cross resulting in this new variety was made during 2019.

The seed parent is an unnamed, unpatented, proprietary *Ranunculus asiaticus*. The pollen parent is an unnamed, unpatented, *Ranunculus cortusifolius*. The new variety was selected in 2021 by the inventor in a group of seedlings resulting from the 2019 crossing, in a research greenhouse in Camporosso Mare, Italy.

Asexual reproduction of the new cultivar was first performed by vegetative division of buds sprouting from the rhizome of the selected plant. Subsequent propagation has been performed by tissue culture. First propagation took place at a research greenhouse in Camporosso Mare, Italy in 2021 and has shown that the unique features of this cultivar are stable and reproduced true to type in multiple successive generations.

SUMMARY OF THE INVENTION

The cultivar 'BC ALIGAX' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BC ALIGAX'. These characteristics in combination distinguish 'BC ALIGAX' as a new and distinct *Rammculus* cultivar:

1. Novel flower: well branched flower stems and double daisy like flower.
2. Pale Yellow Green RHS 157A and 157B flower color.
3. Vegetative, herbaceous plant habit.
3. 6 to 20 cm long flower stems.

PARENT COMPARISON

Plants of the new cultivar 'BC ALIGAX' are similar to plants of the seed parent, in most horticultural characteristics, however, plants of the new cultivar 'BC ALIGAX' differ in the following;

1. Flower petals of the new cultivar are pale yellow green RHS 157A and 157B; flower petals of the seed parent are white.
2. The seed parent does not have the novel flower stem branching and double-daisy type flower of the new cultivar.

Plants of the new cultivar 'BC ALIGAX' are similar to plants of the pollen parent, in most horticultural characteristics, however, plants of the new cultivar 'BC ALIGAX' differ in the following;

1. Flower petals of the new cultivar are pale yellow green RHS 157A and 157B; flower petals of the pollen parent are yellow colored.
2. The pollen parent has a single daisy type flower, with only 5 petals; the new cultivar has a double daisy flower form with about 30 to 60 petals.

COMMERCIAL COMPARISON

Plants of the new cultivar 'BC ALIGAX' are comparable to the cultivar *Ranunculus* 'BC UALLABI', co-pending application Ser. No. 19/357,296. The two *Ranunculus* varieties are similar in most horticultural characteristics; however, the new variety 'BC ALIGAX' differs in the following:

1. Petal color of the new cultivar is pale yellow green RHS 157A and 157B; petal color of this comparator is strong pink RHS 49A.

BRIEF DESCRIPTION OF THE PHOTOGRAPHS

The accompanying photograph in FIG. 1 illustrates in full color a close-up view of a flowering stem of the new cultivar. The plant producing this flower stem was approximately six months old, grown in a greenhouse during March in Camporosso, Italy.

Figure 1:
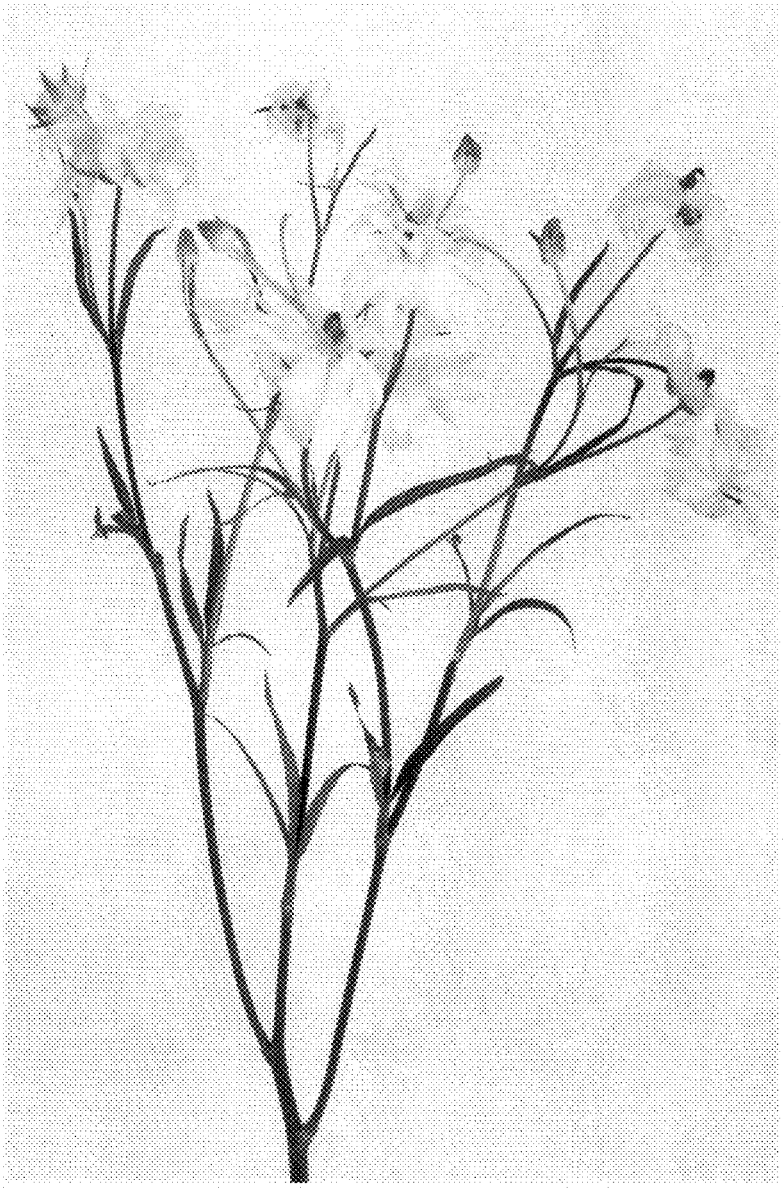
Figure 2:
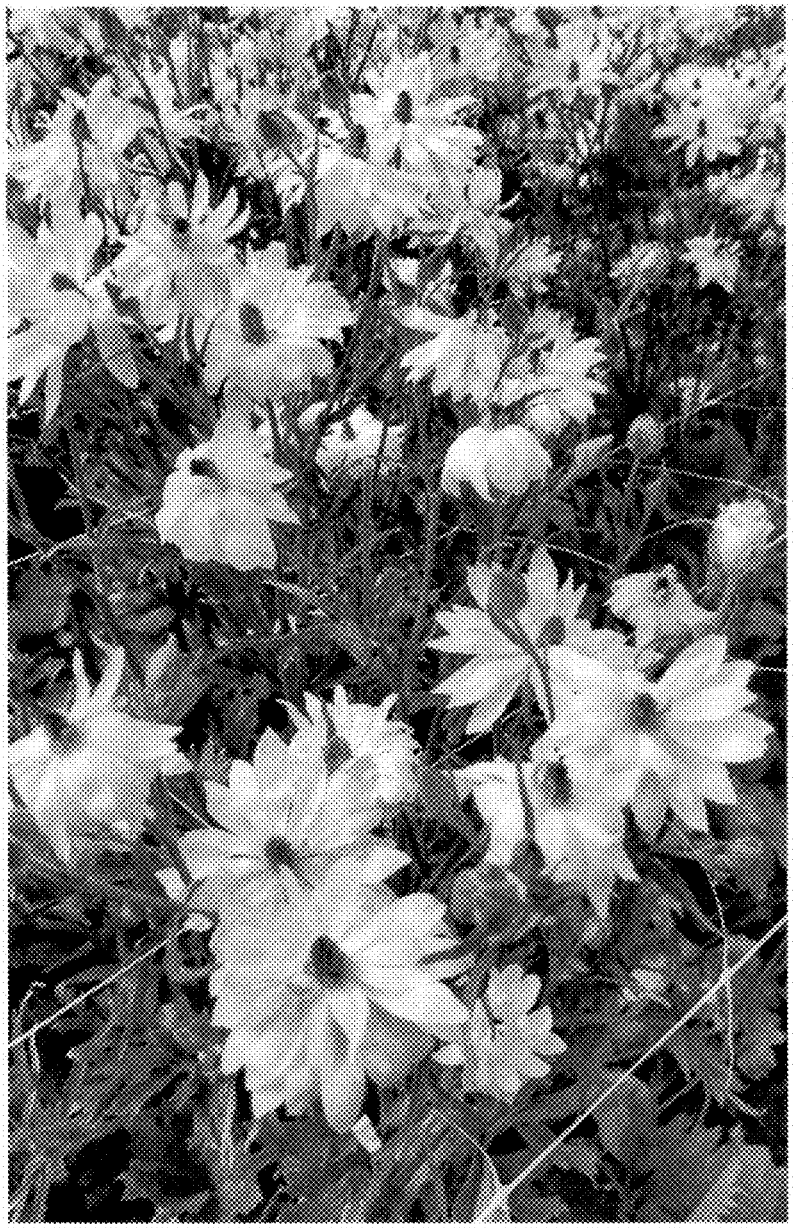
FIG. 2 illustrates plants of about 6 months old in commercial greenhouse production.
Figure 3:
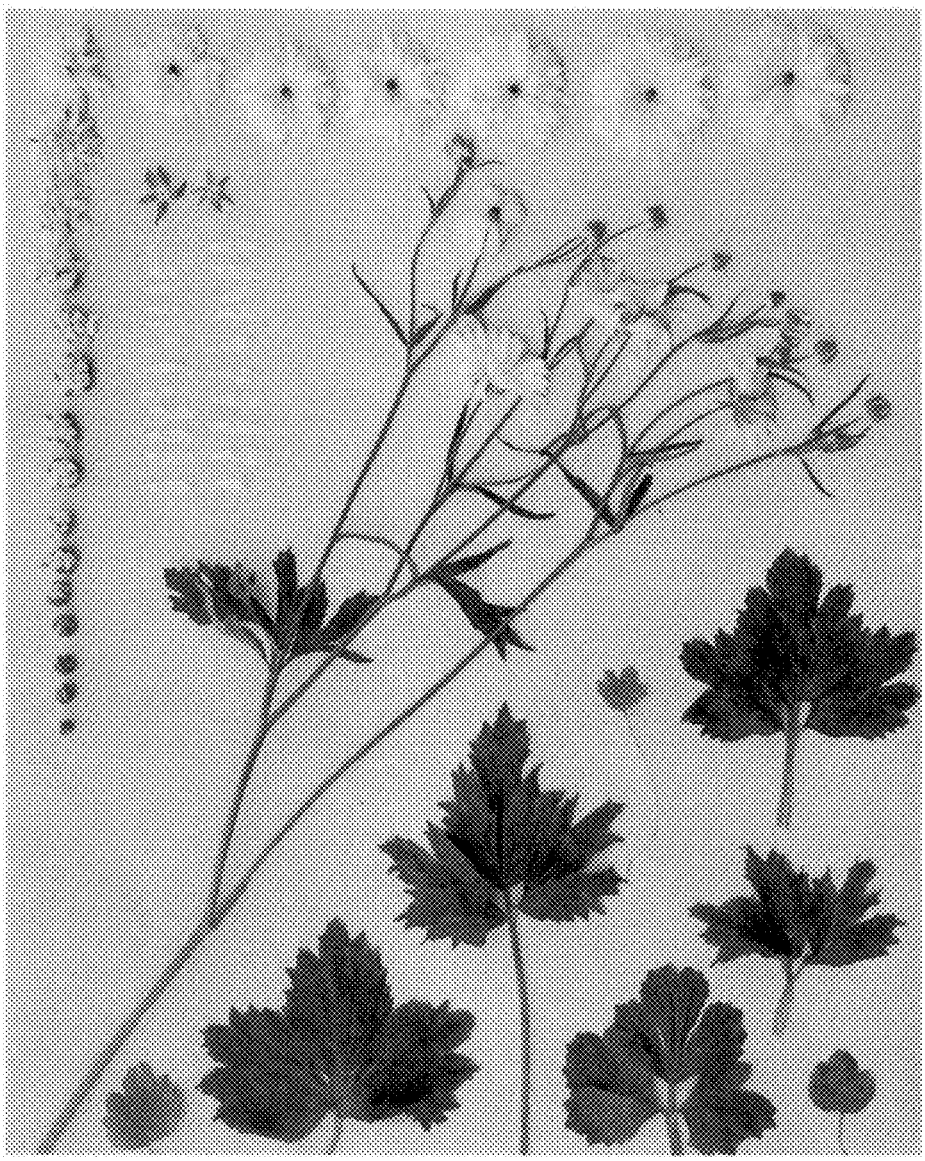
FIG. 3 illustrates various floral and foliar parts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe plants of 'BC ALIGAX' planted in the month of August in a greenhouse in Camporosso Mare, Italy. The plant has been described in the month of March. In order to protect the crop against pests, some chemical treatments are performed. Treatments with growth regulators can be performed to limit the plant sizes. No growth regulators have been applied on the plant described. The rhizome has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* x *cortusifolius* 'BC ALIGAX'.

PROPAGATION

Time to rooting: 15 days at approximately 10-12° C.

Time to produce a rooted plantlet: 20 days.

Root description: Secondary roots grow by rhizome and are fasciculate type.

PLANT

Age of the plant described: About 5 months.

Growth habit: Herbaceous perennial, robust plant, semi-prostrate vegetation.

Height to top flower: 50 to 95 cm.

Plant spread: 40 to 60 cm.

Branching characteristics: The main flower stem emerges from a basal rosette and divides into two primary branches. Each of these produces 2-3 secondary branches, which continue to branch in a similar pattern, with each final branch ending in a flower.

Length of lateral branches: 30 to 60 cm.

Diameter of lateral branches: 0.3 to 0.7 cm.

Texture of Lateral Branches: Ciliate and slightly tomentose.

Internode length: 6 to 12 cm.

Strength of lateral branches: Moderate.

Color of lateral branches: Strong Yellow Green (RHS 144A).

Angle of branches: 25° to 30°.

Number of leaves per lateral branch: Usually 2 to 4.

FOLIAGE

Plants have marked heterophyllia in relation to the degree of their development and their position on the plant (base of the plant; floral stem). The same plant may have leaves of different size and arrangement (simple, ternate and biternate), in relation to the degree of development (young leaf and mature leaf) and their position on the plant.

Leaf at the base of the plant:

*Arrangement*.—Simple-Biternate young leaf; Biternate mature leaf.

*Average length*.—4-20 cm.

*Average width*.—4-25 cm.

*Overall shape of blade*.—Obovate (young leaf); Palmatipartite (mature leaf).

*Dissected leaves, describe Lobes, quantity of dissection*.—The young leaves are generally not lobed, while the mature leaves are typically divided into 3 sections, each of which is further subdivided into 3 lobes.

*Apex*.—Acute.

*Base*.—Attenuate.

*Attachment*.—Petiolate.

*Margin*.—Dentate.

*Texture of top surface*.—Slightly tomentose.

*Texture of bottom surface*.—Slightly tomentose.

*Appearance of top surface*.—Glossy.

*Appearance bottom surface*.—Glossy.

*Leaf internode length*.—The internodes are extremely close together, forming a basal rosette.

*Color*.—Young foliage upper side: Moderate Olive Green (RHS 137A). Young foliage under side: Moderate Yellow Green (RHS 146B). Mature foliage upper side: Moderate Olive Green (RHS 137A). Mature foliage under side: Moderate Yellow Green (RHS 146B).

*Venation*.—Type: Dichotomous; plunging into the limb at the upper surface; raised on the limb at the lower surface. Venation color upper side: Strong Yellow Green (RHS 144B). Venation color under side: Strong Yellow Green (RHS 144AB and 144C).

*Petiole*.—General description: Tubular and rigid. Length: 15-40 cm. Diameter: 0.4-0.8 cm. Pubescence: Slightly tomentose. Color: Strong Yellow Green (RHS 144C).

Leaf inserted at the nodes of the floral stems:

*Arrangement*.—Biternate.

*Average length*.—10-20 cm.

*Average width*.—12-20 cm.

*Overall shape of blade*.—Palmatipartite.

*Dissected leaves, describe lobes, quantity of dissection*.—Generally divided into 3 parts, each one of which is further divided into 3 more lobes.

*Apex*.—Acute.

*Base*.—Attenuate.

*Attachment*.—Petiolate.

*Margin*.—Dentate.

*Texture of top surface*.—Slightly tomentose.

*Texture of bottom surface*.—Slightly tomentose.

*Appearance of top surface*.—Glossy.

*Appearance bottom surface*.—Glossy.
*Leaf internode length*.—10-20 cm.
*Color*.—foliage upper side: Moderate Olive Green (RHS 137A). foliage under side: Moderate Yellow Green (RHS 146B).
*Venation*.—Type: Dichotomous, plunging into the limb at the upper surface and raised on the limb at the lower surface. Venation color upper side: Strong Yellow Green (RHS 144B). Venation color under side: Strong Yellow Green (RHS 144B and 144C).
*Petiole*.—General Description: Slightly flat, rigid. Length: 3-10 cm. Diameter: 0.5-1.0 cm. Pubescence: Slightly tomentose. Color: Strong Yellow Green (RHS 144C).

FLOWER

Bloom period: Winter-Spring.
Vase life (cut flower): 10-15 days.
Persistent or self-cleaning: Self-Cleaning.
Bud:
*Closed bud*.—Shape: Globular with an acute apex. Length: 1-2 cm. Diameter: 0.5-1.5 cm. Color: Sepals are Strong Yellow Green (RHS 144A); Pale Yellow Green (RHS 157B) when sepals start to overlap and it's possible to see the young petals.
*Slightly open bud*.—Shape: Globular with an acute apex. Length: 1.0-1.5 cm. Diameter: 1.0-1.7 cm. Color: Pale Yellow Green (RHS 155A); Moderate Red (RHS 183D) at the apex.
Flower size:
*Diameter*.—4-10 cm.
*Height*.—1-2 cm.
Corolla: Round, symmetrical, flattened.
*Petals*.—
*Arrangement*.—Radially symmetrical, regular, actinomorphic.
*Petal length*.—1.5-5 cm.
*Petal width*.—0.4-1.5 cm.
*Quantity*.—Double flower, 30 to 60.
*Texture*.—Silky. Resistant to tearing.
*Petal apex*.—Acute.
*Petal base*.—Attenuate.
*Petal shape*.—Oblanceolate.
*Margin*.—Entire and slightly undulate.
*Aspect*.—Mostly flat.
*Color when opening*.—
*Upper surface*.—Pale Yellow Green (RHS 157A and 157B).
*Lower surface*.—Pale Yellow Green (RHS 157C); Moderate Red (RHS 183D) at apex.
*Color fully opened*.—
*Upper surface*.—Pale Yellow Green (RHS 157A to 157B).
*Lower surface*.—Pale Yellow Green (RHS 157C); Moderate Red (RHS 183D) at apex.
Calyx—Sepals:
*Quantity per flower*.—6.
*Shape*.—Concave incurved at the apex.
*Length*.—1-2 cm.
*Width*.—0.5-0.7 cm.
*Apex*.—Acute.
*Base*.—Truncate.
*Margin*.—Entire.
*Texture*.—Slightly tomentose all surfaces.
*Color upper surface*.—Strong Yellow Green (RHS 143A and 144A).
*Color lower surface*.—Strong Yellow Green (RHS 143C).
Peduncle: None.
Pedicel:
*Length*.—6-20 cm.
*Diameter*.—0.1-0.6 cm.
*Color*.—Strong Yellow Green (RHS 144A).
*Orientation*.—Upright. Straight.
*Pubescence*.—Slightly tomentose.
Fragrance: None.

REPRODUCTIVE ORGANS

Androecium: Stamens are almost completely transformed to petals. Very infrequently small, malformed stamens can be found in some flowers at the end of the flowering.
Gynoecium: The pistils are numerous, short, locked together at the center of the corolla in a Dark Red (RHS 187A) or Greyish Purple (RHS N187B) cone-shaped apocarpous gynoecium.
Nectar glands: Absent.

OTHER CHARACTERISTICS

Disease and pests: Neither resistance nor susceptibility observed.
Drought tolerance and cold tolerance: No differences have been noted in comparison to the common tolerance characteristics to other *Ranunculus* cultivars.
Fruit—Seed production: Not observed.

What is claimed is:
1. A new and distinct cultivar of *Ranunculus* plant named 'BC ALIGAX' as herein illustrated and described.

* * * * *